(12) United States Patent
Martin et al.

(10) Patent No.: US 6,946,426 B2
(45) Date of Patent: Sep. 20, 2005

(54) PROCESS TO PREPARE AQUEOUS FORMULATIONS

(75) Inventors: Timothy M. Martin, Ringoes, NJ (US); MaryEllen Lavin, Paramus, NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 10/221,759

(22) PCT Filed: Mar. 21, 2001

(86) PCT No.: PCT/US01/09140

§ 371 (c)(1), (2), (4) Date: Feb. 10, 2003

(87) PCT Pub. No.: WO01/70024

PCT Pub. Date: Sep. 27, 2001

(65) Prior Publication Data

US 2003/0211128 A1 Nov. 13, 2003

Related U.S. Application Data

(60) Provisional application No. 60/191,280, filed on Mar. 22, 2000.

(51) Int. Cl.$^7$ .................. A01N 25/22; A01N 43/653; A01N 43/80; A01N 57/00; A01N 53/06

(52) U.S. Cl. .................. 504/139; 504/118; 504/127; 504/129; 504/130; 504/131; 504/132; 504/133; 504/134; 504/135; 504/136; 504/138; 504/141; 504/142; 504/143; 504/144; 504/145; 504/146; 504/147; 504/148; 504/149; 504/270; 504/273; 504/362; 504/363; 504/365; 514/378; 514/380; 514/384; 514/519; 514/520; 514/521; 514/522; 514/523; 514/524; 514/531; 514/772; 514/772.3; 514/937; 514/938; 514/939; 514/940; 514/941; 514/942; 514/943; 514/970; 514/973

(58) Field of Search .................. 504/118, 127, 504/129–135, 136, 138–139, 141–149, 270, 273, 362, 363, 365; 514/378, 380, 384, 519–524, 531, 772, 772.3, 937–943, 970, 973

(56) References Cited

U.S. PATENT DOCUMENTS

| | | |
|---|---|---|
| 5,125,958 A | 6/1992 | Poss |
| 5,334,585 A | 8/1994 | Derian et al. |
| 5,935,905 A | 8/1999 | Mito |
| 6,127,318 A * | 10/2000 | Sato et al. .................. 504/128 |

FOREIGN PATENT DOCUMENTS

| | | |
|---|---|---|
| WO | WO 90/07277 | 7/1990 |
| WO | WO 99/51099 | 10/1999 |
| WO | WO 00/10392 | 3/2000 |
| WO | WO 00/78139 | 12/2000 |

OTHER PUBLICATIONS

McCutcheon's Emulsifiers & detergents, North American Edition, The Manufacturing Confectioner Publishing Co., NJ, 1996, vol. 1, p. 185.*

* cited by examiner

*Primary Examiner*—John Pak
(74) *Attorney, Agent, or Firm*—FMC Corporation

(57) ABSTRACT

Provided is a method of formulating hydrophobic pesticides comprising emulsifying an aqueous phase and a water-immiscible phase to form a formulation; wherein the aqueous phase is comprised of water and optionally a freeze/thaw agent, one or more emulsifiers, or combinations thereof, and the water-immiscible phase comprises the hydrophobic pesticide and one or more emulsifiers.

15 Claims, No Drawings

PROCESS TO PREPARE AQUEOUS FORMULATIONS

This application is a 371 of PCT/US01/09140, filed on Mar. 21, 2001, which claims benefit of Provisional Application 60/191,280, filed on Mar. 22, 2000.

The present invention relates to the field of agrochemical formulations. In particular, the invention provides aqueous formulations of hydrophobic pesticides that are stable and equally effective as compared with conventional formulations.

Hydrophobic pesticides are commonly formulated as dry formulations because of their immiscibility in water. For example, U.S. Pat. No. 5,125,958 ("US '958") discloses that the herbicide, ethyl 〈-2-dichloro-5-[4-(difluoromethyl)-4,5-dihydro-3-methyl-5-oxo-1H-1,2,4-triazol-1-yl]4-fluorobenzenepropanoate (carfentrazone-ethyl), a viscous, oily liquid, may be formulated as granules of relatively large particle size, as powdery dusts, as wettable powders, as emulsifiable concentrates, as solutions, or as any of several other known types of formulations. In addition, US '958 also discloses that carfentrazone-ethyl may be formulated as water-soluble or water-dispersible granules in which the water serves as a means for applying the formulation rather than as a component of the formulation. Furthermore, U.S. Pat. No. 5,935,905 ("US '905) claims a dry formulation of carfentrazone-ethyl and N-(phosphonomethyl)glycine (glyphosate). Both US '958 and '905 require absorbing the technical grade carfentrazone-ethyl on to a carrier in order to formulate the carfentrazone-ethyl. Although the formulations were intended to have a long shelf life, it has been found that they tend to hydrolyze and as such tend not to be stable. As a result, a need exists to develop formulations of hydrophobic pesticides, in particular carfentrazone-ethyl, that exhibit greater stability.

SUMMARY OF THE INVENTION

The present invention provides new pesticide formulations that are aqueous, economical, environmentally friendly, and exhibit little or no hydrolysis over time thus resulting in enhanced stability characteristics of the pesticidal activity. By reducing or minimizing the use of organic solvents, the costs and dangers associated with the recycling of such materials are avoided. In addition, the process can be conducted in relatively simple equipment using relatively simple process steps.

In one embodiment, the present invention provides pesticidally effective, stable, aqueous formulations of hydrophobic pesticides.

According to one aspect of the invention, the formulation comprises an aqueous emulsion (EW), which is composed of an aqueous phase composed of water and optionally a freeze/thaw agent, one or more emulsifiers, or combinations thereof, and a water-immiscible phase composed of a hydrophobic pesticide and one or more emulsifiers.

According to another aspect of the invention, a pesticidal formulation of a hydrophobic pesticide is provided, which comprises the aforementioned aqueous formulation in combination with one or more additional pesticides.

Also provided in accordance with the present invention are processes for making the aforementioned aqueous emulsions (EW) or pesticidal formulations of the aforementioned aqueous formulation in combination with one or more additional pesticides.

Definitions

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, an organic chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated the substituent terms "alkyl", "cycloalkyl", "alkoxy", "aryloxy", and "alkoxyarylamino", used alone or as part of a larger moiety, includes straight or branched chains of at least one or two carbon atoms, as appropriate to the substituent, and preferably up to 20 carbon atoms, more preferably up to ten carbon atoms, most preferably up to seven carbon atoms. "Halogen" or "halo" refers to fluorine, bromine, iodine, or chlorine. "Aryl" refers to an aromatic ring structure having 5 to 10 carbon atoms. The term "ambient temperature" as utilized herein shall mean any suitable temperature found in a laboratory or other working quarter, and is generally not below about 15° C. nor above about 30° C.

The term "aqueous phase" as used herein refers to water or a mixture of water and a hydrocarbon solvent that is easily emulsified in water. Preferably, the aqueous phase is comprised of at least about 50% v/v, more preferably about 95% v/v, of water.

As used in this specification and unless otherwise indicated the term "pesticide" refers to a molecule or combination of molecules that repels, retards, or kills pests, such as, but not limited to, deleterious or annoying insects, weeds, worms, fungi, bacteria, and the like, and can be used for crop protection, edifice protection, turf protection, or protection of a person; pesticide as used herein includes, but is not limited to, herbicides, insecticides, acaricides, fungicides, nematicides, ectoparasiticides, and growth regulators, either used to encourage growth of a desired plant species or retard growth of an undesired pest.

DETAILED DESCRIPTION OF THE INVENTION

Generally, the present invention relates to aqueous formulations of a hydrophobic pesticide comprising emulsifying an aqueous phase and a water-immiscible phase to form the formulation; wherein water-immiscible phase comprises the pesticide and one or more suitable emulsifiers. Preferably, the aqueous phase includes a suitable freeze/thaw agent or one or more suitable emulsifiers, or a combination thereof. Examples of hydrophobic pesticides that can be used in the present invention include, but are not limited to, carfentrazone-ethyl, sulfentrazone, clomazone, permethrin, zetacypermethrin, and bifenthrin. A preferred hydrophobic pesticide formulated by the present invention is carfentrazone-ethyl.

The formulations of the present invention are believed to prevent or retard hydrolysis of the pesticide. As such, they exhibit equivalent, if not greater, stability than formulations disclosed in the art. In addition, the formulations of the present invention provide a homogeneous dispersion of the hydrophobic pesticide throughout the formulation.

In one embodiment of the present invention, the aqueous phase is added to the water-immiscible phase. That is to say, the formulation is prepared by the following steps:

a) providing the aqueous phase comprised of water;
b) providing the water-immiscible phase containing the hydrophobic pesticide and one or more emulsifiers;
c) adding the aqueous phase to the water-immiscible phase; and,
d) emulsifying the resulting mixture to form the formulation.

In another embodiment of the present invention, the water-immiscible phase is added to the aqueous phase. That is to say, the formulation is prepared by the following steps:
e) providing the water-immiscible phase containing the hydrophobic pesticide and one or more emulsifiers;
f) providing the aqueous phase comprised of water;
g) adding the water-immiscible phase to the aqueous phase; and
h) emulsifying the resulting mixture to form the formulation.

The emulsification is preferably carried out at a temperature in the range of about 20° C. to about 80° C., more preferably from about 20° C. to about 70° C. Preferably the emulsification is carried out for a period of in excess of about three minutes; and in one embodiment for a period of up to about 24 hours; more preferably from about five minutes to about three hours. The emulsification may be carried out at lower temperatures, such as, for example below 15° C., but generally will require an appreciably longer time to complete.

Suitable emulsifiers that may be used in the context of the present invention are those substances that are active at an oil and water interface and which serve to reduce the surface tension of an oil thus allowing for the formation of a stable and homogeneous mixture. Examples of emulsifiers that can be used include, but are not limited to, carboxylates, sulphates, sulphonates, alcohol ethoxylates, alkyl phenol ethoxylates, fatty acid ethoxylates, sorbitan esters, ethoxylated fats or oils, amine ethoxylates, phosphate esters, ethylene oxide—propylene oxide copolymers, fluorocarbons, and silicon polymers. Preferred emulsifiers that can be used are an alkyd-polyethylene glycol resin, a polyalkylene glycol ether, a polyalkoxylated nonyl phenyl, an alkoxylated primary alcohol, an ethoxylated distyrylphenol, an ethoxylated distyrylphenol sulphate, an ethoxylated tristyrylphenol phosphate, a tristyrylphenol phosphate ester, a hydroxylated stearic acid polyalkylene glycol polymer, and their corresponding salts. Particularly preferred emulsifiers that can be used in the present invention are an alkyd-polyethylene glycol resin, a polyalkylene glycol ether, an ethoxylated distyrylphenol, an ethoxylated distyrylphenol sulphate, an ethoxylated tristyrylphenol phosphate, a tristyrylphenol phosphate ester, and a tristyrylphenol phosphate potassium salt.

In yet another embodiment of the present invention, the aqueous phase can contain a freeze/thaw agent and one or more emulsifiers. Examples of freeze/thaw agents, also referred to as cryoprotectants, that can be used in the present invention include, but are not limited to, monoethlyene glycol, propylene glycol, glycerol, urea, and inorganic salts. A preferred freeze/thaw agent used is propylene glycol. The emulsifiers disclosed above may also be included in the aqueous phase. A preferred emulsifier employed in the aqueous phase is an ethylene oxide-propylene oxide copolymer.

In one embodiment of the present invention, the water-immiscible phase can also contain a hydrocarbon solvent. Suitable hydrocarbon solvents are those liquids in which the water-immiscible phase may be miscible. Examples of hydrocarbon solvents that can be used in the present invention, include but are not limited to, alkylated naphthalene aromatics, alkylated biphenyls, hydrogenated aliphates, isoparaffins, paraffins, cycloparaffins, xylene range aromatics, alkyl acetates, fatty acids, esters, mineral and vegetable oils, and olefins. Preferred hydrocarbon solvents that can be used in the present invention are alkylated naphthalene aromatics and alkylated biphenyls.

A typical recipe according to the present invention will ordinarily contain from about 1 to about 50, preferably about 2 to about 30, weight percent of the pesticide, from about 10 to about 25, preferably about 5 to about 10, total weight percent of one or more emulsifiers, and from about 30 to about 80, preferably about 30 to about 75, weight percent of water. An alternative preferred embodiment of the present invention contains about 2 to about 15, preferably about 4 to about 10, weight percent of a freeze/thaw agent in addition to the aforementioned typical recipe. A further preferred alternative embodiment further contains about 1 to about 50, preferably about 4 to about 25, weight percent of a hydrocarbon solvent in addition to the aforementioned typical recipe. Yet another preferred embodiment combines the aforementioned typical recipe, the freeze/thaw agent, and the hydrocarbon solvent, each in the aforementioned concentrations. One further preferred embodiment is a formulation that contains the aforementioned ingredients of the typical recipe, with or without the freeze/thaw agent, with or without the hydrocarbon solvent, plus any other suitable ingredient, such as, without limitation, a second pesticide, a biocide, a thickening agent, and like ingredients commonly found in pesticidal formulations known in the art, many of which are set forth herein below.

Once formulated, the average size of the particles of the pesticides generally is from about 0.01 $\mu$m to about 100 $\mu$m, preferably from about 0.01 $\mu$m to about 10 $\mu$m. The operating conditions to yield particles of a desired size will depend on a variety of factors, including, where applicable, the temperature at which the emulsification is performed, the addition rate of the reactants, the emulsifying equipment used, the amount of emulsifiers used, and the like. For example, a smaller particle size generally results when more emulsifiers are used and longer emulsifying time is used. In light of the present specification, adjustment to determine the proper conditions to achieve emulsions within the scope of the present invention is well within the skill of the art.

After completion of the emulsification step, additional additives may be added to the formulations. The amounts of post emulsification additives to be added are similar for all embodiments and typically would be selected from one or more of about 0.003 to about 1, preferably about 0.005 to about 0.5, weight percent of an antifoam agent, such as a polydimethyl siloxane; about 0.003 to about 1, preferably about 0.005 to about 0.5, weight percent of a thickener, such as a xantham gum or ethyl or methyl cellulose; about 0.01 to about 0.5, preferably about 0.01 to about 0.1, weight percent of one or more bactericides; up to about 0.05, preferably up to about 0.04, weight percent of an inert dye; and up to about 10 weight percent of one or more surfactants, each weight percent relative to the weight of the formulation after addition of the additives.

The formulations of the present invention can be used alone, or a pesticidally effective amount of the formulation, for example, from about 2 to about 50 weight percent, can be combined with a pesticidally effective amount, for example, from 50 to 98 weight percent, of one or more additional pesticides to provide a broader spectrum of activity than conventional formulations containing only a single pesticide. Examples of additional pesticides that are useful in the present invention include, but are not limited to, glyphosate, (2,4-dichlorophenoxy)acetic acid (2,4-D), (4-chloro-2-methylphenoxy)acetic acid (MCPA), (RS)-2-(4-chloro-o-tolyloxy)propionic acid (MCPP), isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr. A preferred additional pesticide is glyphosate.

The formulations of the present invention are further illustrated by the procedures shown in the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

This example illustrates one protocol for the preparation of a four grams/liter microemulsion (4 ME) formulation (Formulation A).

A mixture of four grams of 90% pure carfentrazone-ethyl (available from the FMC Corporation), eight grams of an alkylated naphthalene aromatic solvent (Aromatic 200 ND, available from Exxon Chemical Company, Houston Tex.), eight grams of an ethoxylated distyrylphenol containing 15 moles of ethylene oxide (Soprophor DS/15, available from Rhone-Poulenc, Inc. Newark, N.J.), eight grams of an ethoxylated distyrylphenol sulphate containing 15 moles of ethylene oxide (Soprophor DSS/15, available from Rhone-Poulenc, Inc.), and 70 grams of deionized water was mixed by hand at ambient temperature for two minutes to form an emulsion. The emulsion was heated to about 70° C. where it was mixed by hand for two minutes. After this time, the emulsion was cooled to ambient temperature and two grams of an ethoxylated tristyrylphenol phosphate containing four moles of ethylene oxide (Soprophor DV4624, available from Rhone-Poulenc, Inc.) was added. Upon completion of addition, the emulsion was again heated to 70° C. and then mixed by hand for two minutes. At the conclusion of this period, the emulsion was cooled to ambient temperature to yield the microemulsion.

EXAMPLE 2

This example illustrates one protocol for the preparation of a 240 grams/liter emulsion (240 EW) formulation (Formulation B).

A mixture of 95.3 grams of water, 15 grams of a polyalkylene glycol ether (Atlas G-5000, available from Imperial Chemical Industries (ICI), Bayonne, N.J.), and 10.5 grams of propylene glycol was heated to 70° C. to effect dissolution. In a separate mixing vessel, a mixture of 59.25 grams of 91% pure carfentrazone-ethyl, 60 grams of an alkylated naphthalene aromatic solvent (Solvesso 200, available from the Exxon Chemical Company), and 10 grams of an alkyd-polyethylene glycol resin (Atlox® 4914, available from ICI) was heated to 55° C. and mixed by hand for five minutes. After this time, the above-prepared aqueous propylene glycol solution was added during a 30 second period using a Polytron A3000 mixer (available from Brinkmann Instruments, Inc., Westbury, N.Y.). The resulting mixture was heated to about 55–65° C. and mixed for twenty minutes. At the conclusion of this period, an additional 10 grams of an alkyd-polyethylene glycol resin (Atlox® 4914, available from ICI) was added over a two-minute period while maintaining the temperature at 55° C. Upon completion of addition, the mixture was cooled to 30° C. and mixed for two minutes at 300 rpm to yield the emulsion.

EXAMPLE 3

This example illustrates one protocol for the preparation of a 240 grams/liter emulsion (240 EW) formulation (Formulation C).

This formulation was prepared in the manner of Example 2 with the exception that the emulsification occurred at 50° C. rather than 55° C.

EXAMPLE 4

This example illustrates one protocol for the preparation of a carfentrazone-ethyl and glyphosate formulation (Formulation D).

A mixture of 39.6 grams of a 240 EW carfentrazone-ethyl formulation prepared in the manner of Example 2 and 60.4 grams of N-phosphonomethyl)glycine (glyphosate) (available from Monsanto Company, St. Louis, Mo.) was mixed in a one liter beaker for five minutes at 600 rpm using a Model LiU08 Mixer (available from Lightnin, Rochester, N.Y.).

EXAMPLE 5

This example illustrates one protocol for the preparation of a 240 grams/liter emulsion (240 EW) formulation (Formulation E).

Carfentrazone-ethyl, 90.6% pure, 221.44 grams, was heated to about 40–45° C., and 24 grams of bis(-methylethyl)-1,1'-biphenyl (available as NuSolv™ ABP-103 from Ridge Technologies, Inc., Ridgewood, N.J.) and 16 grams of epoxidized soybean oil (available as Drapex® 6.8 from Witco Corp., Oakland, N.J.) were added. Upon completion of addition, the mixture was mixed for five minutes using a Kitchen Aid Type mixer and then 96 grams of a mixture of monohydrogen and dihydrogen tristyrylphenol phosphate esters and the corresponding potassium salt (available as Soprophor FLK-40 from Rhone-Poulenc, Inc.) and 16 grams of a nonionic ethoxylated tristyrylphenol (available as Soprophor BSU from Rhone-Poluenc, Inc.) were added. The resulting mixture was stirred for five minutes. After this time, 356.6 grams of 45° C. warm water was added during a five minute period followed by 80 grams of an aqueous solution containing 2% of a xantham gum (available as Rhodopol 23 from R.T. Vanderbilt Co., Inc. Norwalk, Conn.) and 0.1% of an antimicrobial biocide (available as Legend MK™ from Rohm and Haas Co., Philadelphia, Pa.). Upon completion of addition, the resulting mixture was mixed for two hours at 400 rpm to yield the emulsion.

EXAMPLE 6

This example illustrates one protocol for the preparation of a 240 grams/liter emulsion (240 EW) formulation (Formulation F).

This formulation was prepared in the manner of Example 5 with the exception that the emulsification and water temperatures were 40° C. rather than 45° C.

EXAMPLE 7

This example illustrates one protocol for the preparation of a four grams/liter microemulsion (4 ME) formulation (Formulation G).

A mixture of five grams of 91.8% pure carfentrazone-ethyl, five grams of an alkylated naphthalene aromatic solvent (Aromatic 200 ND), 1.5 grams of a proprietary combination of emulsifiers identified as Sponto 4289, RDB 10/168 (available from Witco Corp.), and 13.5 grams of a proprietary combination of emulsifiers identified as Sponto 4290, RDB 10/164 (also available from Witco Corp.) was heated to about 40° C. where it was mixed by hand for two minutes. After this time, 75 grams of deionized water was added to yield an emulsion. Upon completion of addition, the emulsion was again heated to 40° C and then mixed by hand for two minutes. At the conclusion of this period, the emulsion was cooled to ambient temperature to yield the microemulsion.

EXAMPLE 8

This example illustrates one protocol for the preparation of a 240 grams/liter emulsion (240 EW) formulation (Formulation H).

To a mixture of 28 grams of permethrin, 4 grams of bis(-methylethyl)-1,1'-biphenyl (NuSolv™ ABP-103) and 2 grams of epoxidized soybean oil (Drapex® 6.8) was added 12 grams of a mixture of monohydrogen and dihydrogen tristyrylphenol phosphate esters and the corresponding potassium salt (Soprophor FLK-40) and 16 grams of a nonionic ethoxylated tristyrylphenol (Soprophor BSU). Upon completion of addition, the mixture was mixed at ambient temperature for twenty minutes using a Kitchen Aid Type mixer. After this time, 44.5 grams of water was added followed by 7.5 grams of an aqueous solution containing 2% of a xantham gum (Rhodopol 23). Upon completion of addition, the resulting mixture was mixed for two hours at 400 rpm to yield the emulsion.

EXAMPLE 9

This example illustrates one protocol for the preparation of a 240 grams/liter emulsion (240 EW) formulation (Formulation J).

This formulation was prepared in the manner of Example 8 with the exception that zetacypermethrin rather than permethrin was formulated.

EXAMPLE 10

This example illustrates one protocol for the preparation of a 400 grams/liter emulsion (400 EW) formulation (Formulation K).

A mixture of 219.5 grams of water, 28.75 grams of a polyalkylene glycol ether (Atlas G-5000), and 0.5 gram of a 100% polydimethyl siloxane antifoam agent (Dow Corning® 1520, Dow Corning Corporation, Midland, Mich.) was heated to 50° C. to effect dissolution. In a separate mixing vessel, a mixture of 210.65 grams of 91.3% pure clomazone, 19.35 grams of an alkylated naphthalene aromatic solvent (Aromatic 200 ND), and 21.25 grams of an alkyd-polyethylene glycol resin (Atlox® 4914) was heated to 50° C. to effect dissolution and then mixed by hand for five minutes. After this time, the above-prepared aqueous antifoam agent solution was added using a Silverson L4RT mixer (available from Silverson Machine LTD., England). The resulting mixture was cooled to 30–40° C and mixed for eighteen minutes at 3000–7000 rpm to yield the emulsion. At the conclusion of this period, the mixture was stirred for one hour at 300 rpm to yield the emulsion.

EXAMPLE 11

This example illustrates one protocol for the preparation of a 100 grams/liter emulsion (240 EW) formulation (Formulation L).

A stirred mixture of 128.4 grams of bifenthrin and 447.6 grams of an alkylated naphthalene aromatic solvent (Aromatic 200 ND) was heated to 50° C. to effect dissolution. In a separate mixing vessel, a mixture of 443.4 grams of water, 60 grams of a polyalkylene glycol ether (Atlas G-5000), 0.6 gram of an antimicrobial biocide (Legend MK™), and 72 grams of propylene glycol was mixed for ten minutes using a Silverson L4RT mixer. After this time, the above-prepared bifenthrin solution was added during a five-minute period at 5600 rpm using a Silverson L4RT mixer. The resulting mixture was mixed for twenty minutes. At the conclusion of this period, 48 grams of an alkyd-polyethylene glycol resin (Atlox® 4914) was added over a five-minute period at 3600 rpm using a Silverson L4RT mixer. Upon completion of addition, the mixture was mixed and allowed to cool to ambient temperature to yield the emulsion.

EXAMPLE 12

Stability Studies

This example sets forth stability studies that were accomplished on formulations prepared in accordance with the present invention.

Laboratory tests that show the stability of the emulsion (EW) formulations were carried out in the following manner. Prior to commencing the stability tests, an initial percentage of active ingredient (carfentrazone-ethyl) present in Formulations C, E, and F prepared above was determined by chromatographic techniques. After this determination, the formulations were stored at 54° C. for periods of two weeks, one month, and three months. After each of these periods, the percentage of active ingredient present in the formulation was determined by the same chromatographic technique. The results of these tests are presented in Table 1 below.

| | Percentage of Active Ingredient Present[1] | | | | | |
|---|---|---|---|---|---|---|
| Formulation | C | | E | | F | |
| Temperature | A.T.[2] | 54° C. | A.T. | 54° C. | A.T. | 54° C. |
| initial Pull | 21.6 | — | 24.7 | — | 25.0 | — |
| 2-week Pull | — | 22.4 | — | 23.5 | — | — |
| 1 month Pull | 22 | 22.4 | — | 24.6 | 25.2 | 24.7 |
| 3 month Pull | 21.7 | 22 | | 24.3 | 25.3 | 24.5 |

[1]Average of two Replicates
[2]Ambient Temperature

The results, shown in Table 1, indicate that the EW formulations of the present invention maintained their stability at elevated temperature.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

We claim:

1. A process for preparing a stable, aqueous formulation of a hydrophobic pesticide comprising emulsifying an aqueous phase and a water-immiscible phase sufficient for the homogeneous dispersal of the pesticide throughout the formulation:

a) wherein the water-immiscible phase comprises the hydrophobic pesticide and an alkyd-polyethylene glycol resin; and b) wherein the aqueous phase comprises a polyalkylene glycol ether emulsifier.

2. The process of claim 1, wherein the pesticide is selected from the group consisting of carfentrazone-ethyl, sulfentrazone, clomazone, permethrin, zetacypermethrin, and bifenthrin.

3. The process of claim 2, wherein the pesticide is carfentrazone-ethyl.

4. The process of claim 1, wherein the aqueous phase comprises a freeze/thaw agent selected from the group consisting of monoethlyene glycol, propylene glycol, glycerol, urea, and inorganic salts.

5. The process of claim 1, wherein the water-immiscible phase further comprises a hydrocarbon solvent selected from the group consisting of an alkylated naphthalene aromatic, an alkylated biphenyl, a hydrogenated aliphate, an isoparaffin, a xylene range aromatic alkyl acetate, a fatty acid, an ester, a mineral oil, a vegetable oil, and an olefin.

6. The process of claim 5, wherein the hydrocarbon solvent is alkylated naphthalene aromatic.

7. The process of claim 1, wherein the emulsification comprises stirring the aqueous phase and the water-immiscible phase at a temperature in the range of about 20° C. to about 80° C. for a period of about three minutes to about 24 hours.

8. The process of claim 7, wherein the emulsification comprises stirring the aqueous phase and the water-immiscible phase at a temperature in the range of about 20° C. to about 70° C. for a period of about five minutes to about three hours.

9. A stable, aqueous pesticidal formulation comprising
a) a pesticidally effective amount of a hydrophobic pesticide;
b) a water-immiscible phase comprising the hydrophobic pesticide and an alkyd-polyethylene glycol resin; and
c) an aqueous phase comprising a polyalkylene glycol ether emulsifier.

10. The stable, aqueous pesticidal formulation of claim 9, wherein the pesticide is selected from the group consisting of carfentrazone-ethyl, sulfentrazone, clomazone, permethrin, zetacypermethrin, and bifenthrin.

11. The stable, aqueous pesticidal formulation of claim 10, wherein the pesticide is carfentrazone-ethyl.

12. The stable, aqueous pesticidal formulation of claim 9, further comprising a pesticidally effective amount of one or more additional pesticides selected from the group consisting of glyphosate, (2,4-dichlorophenoxy)acetic acid, (4-chloro-2-methylphenoxy)acetic acid, (RS)-2-(4-chloro-o-tolyloxy)propionic acid, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

13. The stable aqueous pesticidal formulation of claim 9, wherein the aqueous phase comprises a freeze/thaw agent selected from the group consisting of monoethlyene glycol, propylene glycol, glycerol, urea, and inorganic salts.

14. The stable, aqueous pesticidal formulation of claim 9, wherein the water-immiscible phase further comprises a hydrocarbon solvent selected from the group consisting of an alkylated naphthalene aromatic, an alkylated biphenyl, a hydrogenated aliphate, an isoparaffin, a xylene range aromatic alkyl acetate, a fatty acid, an ester, a mineral oil, a vegetable oil, and an olefin.

15. The stable, aqueous pesticidal formulation of claim 14, wherein the hydrocarbon solvent is alkylated naphthalene aromatic.

* * * * *